United States Patent [19]

Adger et al.

[11] Patent Number: 4,515,952

[45] Date of Patent: May 7, 1985

[54] SYNTHESIS OF 2-PYRIDYLALKYLAMINES SUBSTITUTED ON THE PYRIDYL RING BY BROMINE

[75] Inventors: Brian M. Adger, Hildenborough near Tonbridge; David J. O'Rourke, Cobham, both of England

[73] Assignee: Smith Kline & French Laboratories Limited, Welwyn Garden City, England

[21] Appl. No.: 477,037

[22] Filed: Mar. 22, 1983

[30] Foreign Application Priority Data

Mar. 25, 1982 [GB] United Kingdom ............... 8208749

[51] Int. Cl.³ .......................................... C07D 213/61
[52] U.S. Cl. ............................................... 546/329
[58] Field of Search ....................................... 546/329

[56] References Cited

U.S. PATENT DOCUMENTS 4,154,834 5/1979 Brown et al. ..................... 424/251

FOREIGN PATENT DOCUMENTS 0068833 5/1983 European Pat. Off. .
0068834 5/1983 European Pat. Off. .

OTHER PUBLICATIONS van der Does et al., *Recueil*, 84:951–964, (1965).
Mertel, Pyridine and its Derivatives, Interscience, (1961), pp. 316–317.
House, Modern Synthetic Reactions, Benjamin Inc. (1965), pp. 138–139.

*Primary Examiner*—Henry R. Jiles
*Assistant Examiner*—Bernard I. Dentz
*Attorney, Agent, or Firm*—Joan S. Keps; Richard D. Foggio; Alan D. Lourie

[57] ABSTRACT

The invention provides a process for preparing 2-pyridylalkylamines, substituted in one of the 3- or 5-positions by bromo and in the other by $C_{1-4}$ alkyl, by reacting an appropriate $C_{1-4}$ alkyl substituted 2-pyridylalkylamine with an electrophilic brominating agent. Said 2-pyridylalkylamines are useful as intermediates in the synthesis of compounds useful as histamine $H_1$-antagonists.

4 Claims, No Drawings

SYNTHESIS OF 2-PYRIDYLALKYLAMINES SUBSTITUTED ON THE PYRIDYL RING BY BROMINE

This invention relates to processes for preparing certain 3,5-disubstituted-2-pyridylalkylamines.

European Patent Specification No. 0068833 and European Patent Specification No. 0068834 disclose compounds of formula (I):

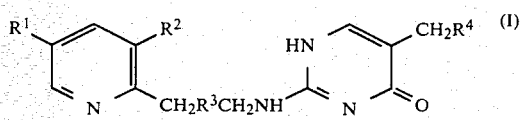

where, in Specification No. 0068833, $R^1$ is halogen or nitro; $R^2$ is $C_{1-4}$ alkyl; in Specification No. 0068834 $R^1$ is $C_{1-4}$ alkyl; $R^2$ is $C_{1-4}$ alkyl, $C_{3-4}$ alkoxy, halogen, or amino; and in both Specifications $R^3$ is $C_{1-3}$ alkylene and $R^4$ represents certain specified substituted and unsubstituted 3- and 4-pyridyl groups. These compounds are useful as histamines $H_1$-antagonists.

The pyridyl alkylamines which can be made by the processes of this invention are useful as intermediates for preparing certain compounds of formula (I).

Accordingly the present invention provides a process for preparing a compound of formula (II):

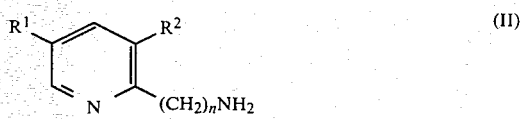

and salts thereof where one of $R^1$ and $R^2$ is $C_{1-4}$ alkyl, the other is bromo, and n is from 3 to 5 which comprises reacting a compound of formula (III):

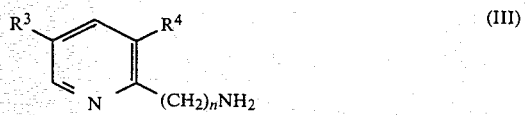

or a salt thereof, where one of $R^3$ and $R^4$ is $C_{1-4}$ alkyl, the other is hydrogen and n is defined with reference to formula (II), with an electrophilic brominating agent.

Examples of electrophilic brominating agents are bromine or dibromocyanuric acid in a polar medium which generates $Br^+$. Examples of such media are oleum and fluorosulphonic acid.

$Br^+$ can also be generated from hydrobromic acid or bromide ion in an oxidizing polar medium. For example hydrobromic acid is oxidized by solutions of sulphur trioxide to bromine. The bromine so formed dissociates giving $Br^+$. The solvent for the sulphur trioxide can be a freon for example 1,1,2-trifluorotrichloroethane or in sulphuric acd. The hydrobromic acid can be derived from the dihydrobromic salt of the compound of formula (III), particularly when the reaction is carried out using sulphur trioxide and freon. Where the sulphur trioxide solution is in sulphuric acid i.e. it is oleum, the hydrobromic acid can be generated from a bromide salt for example an alkali metal salt in particular potassium bromide.

Compounds of formula (III) form neutral complexes with sulphur trioxide. The effect of this is that the pyridine ring in the compounds of formula (III) is activated to bromination. Thus preferably the medium is one which dissolves sulphur trioxide.

Two preferable media for carrying out the bromination reactions are oleum and sulphur trioxide in freon. Where the medium is oleum, in practice it is at least 20% w/w. Preferably it is at least 65% w/w. The more concentrated the oleum, the lower is the temperature at which the reaction can be carried out. For example where the medium is 20% oleum the reaction requires elevated temperatures to proceed in a short period and at this concentration of oleum it is carried out at 100° C. and above. Where the medium is 65% oleum the reaction can be carried out at from 0° C. to 100° C., preferably from 50°–60° C. especially 55°–58° C.

Where the medium is sulphur trioxide in freon the reaction is carried out at from ambient temperature to the reflux temperature of the solvent.

Preferably $R^4$ in the compound of formula (III) is methyl. Preferably n is 4.

The product can be isolated and purified by standard techniques.

The compounds of formula (III):

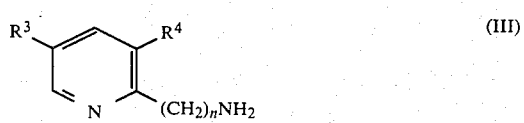

where n, $R^3$ and $R^4$ are as previously defined, can be made by known methods or by reacting an alkali metal derivative of a compound of formula (V):

where $R^3$ and $R^4$ are as defined with reference to formula (III) with a compound of formula (VI):

$$X(CH_2)_{n-1}NH_2 \qquad (VI)$$

or a salt thereof where X is halogen and n is as defined with reference to formula (III).

In the compound of formula (VI), X can be chlorine, bromine or iodine. In particular it is chlorine.

Preferably an acid addition salt of a compound of formula (VI) is used, for example an addition salt with sulphuric or hydrochloric acid. Preferably the salt is the hydrochloride.

The alkali metal derivative can be a lithium, sodium or potassium derivative. In particular it is the sodium derivative.

The alkali metal derivative of compound of formula (V) can be prepared in situ by reacting the compound of formula (V), with an alkali metal amide (in particular sodamide, where the alkali metal is sodium) in which case the solvent is preferably liquid ammonia or an alkyl alkali metal (in particular butyl lithium, where the alkali metal is lithium) in which case the solvent is preferably an ether, for example diethylether or tetrahydrofuran.

The process is carried out at reduced temperatures. For example where the reaction is carried out in liquid ammonia, the temperature is at or below the boiling point of ammonia and where a derivative of formula (V) is generated in situ from an alkyl alkali metal the reaction is carried out at liquid nitrogen temperature, preferably in an inert atmosphere.

The product can be isolated from the reaction mixture by methods analogous to known methods and purified by standard techniques.

The compounds of formula (V) and (VI) are known or can be made by known methods.

The following Examples illustrate the invention.

EXAMPLES

Example 1

(a) 2,3-Lutidine (321 g) was added with stirring to a solution of sodamide (351 g) in liquid ammonia (3 l). 1-Amino-3-chloropropane hydrochloride (429 g) was added to this mixture over 8 minutes with stirring. Any liquid ammonia lost through evaporation was replaced. After 2 hours the reaction was quenched by the addition of ammonium chloride (120 g) and the reaction mixture was left to stand overnight to allow substantially complete escape of ammonia through evaporation. The residue so obtained was diluted with water (2 l) and extracted with dichloromethane. The extracts were dried ($Na_2SO_4$), the dichloromethane removed by evaporation and the residue distilled in vacuo to give 4-(3-methyl-2-pyridyl)butylamine (306.6 g).

(b) Bromine (10 g) was added dropwise with stirring to a solution of 4-(3-methyl-2-pyridyl)butylammonium sulphate (21.3 g) obtained from 4-(3-methyl-2-pyridyl)-butylamine and concentrated sulphuric acid in 65% oleum (100 ml) at room temperature. The solution was then heated to 55° C. and stirred overnight.

The solution was cooled and added slowly to ice (38 g). The resultant solution was poured into water (250 ml) and taken to pH 2.5 with aqueous ammonia solution (s.g. 0.88) and a dibrominated impurity crystallized which was removed by filtration. The filtrate was taken to pH 9.5 and extracted with dichloromethane and the extracts were dried ($MgSO_4$) and decolourised with charcoal.

Acetic anhydride (19 ml) was added to the dried extract and the mixture was heated under reflux for 30 min. After cooling the mixture was washed with water and potassium carbonate solution (56% w/v) which removed any unbrominated starting material. The organic layer was dried ($MgSO_4$) and the solvent evaporated at reduced pressure the residue (18.4 g) heated ca 16 hr. on a steam bath with conc. hydrochloric acid. The solution so obtained was cooled, taken to pH 9.5 with aqueous ammonia solution (s.g. 0.88) and extracted with dichloromethane. The organic phase was dried and the solvent evaporated at reduced pressure to yield 4-(5-bromo-3-methyl-2-pyridyl)butylamine (12.4 g) as a yellow oil which crystallised on being left to stand.

Example 2

(a) Substitution of 2,5-dimethylpyridine (321 g) for 2,3-lutidine in the process of Example 1(a) gives 4-(5-methyl-2-pyridyl)butylamine.

(b) Substitution of 4-(5-methyl-2-pyridyl)butylamine (49.2 g) for 4-(3-methyl-2-pyridyl)butylamine gives 4-(3-bromo-5-methyl-2-pyridyl)butylamine.

Example 3

A solution of sulphur trioxide (150 ml) in 1,1,2-trifluorotrichloroethane (350 ml) was added over ca 30 min. to a suspension of 4-(3-methyl-2-pyridyl)butylamine dihydrobromide (17 g) [prepared by passing hydrogen bromide gas through a solution of the amine in dichloromethane] in 1,1,2-trifluorotrichloroethane (100 ml) and the mixture was heated under reflux for ca 16 hr. The solvent was removed by distillation and unbrominated starting material was removed by acetylation as described in Example 1(b) to yield 4-(5-bromo-3-methyl-2-pyridyl)-butylamine (6.53 g) as an oil.

Example 4

A solution of sulphur trioxide (150 ml) in 1,1,2-trifluorotrichloroethane (550 ml) was added over 30 min to a suspension of 4-(3-methyl-2-pyridyl)butylamine hydrobromide (14.2 g) [prepared by reacting 4-(3-methyl-2-pyridyl)butylamine with hydrobromic acid (0.89M) in 1,1,2-trifluorotrichloroethane and to this mixture was added liquid bromine (5.56 g). The mixture was heated under reflux for ca 16 hr. The solvent was removed by distillation and unbrominated starting material was removed by acetylation as described in Example 1(b) to yield 4-(5-bromo-3-methyl-2-pyridyl)-butylamine (6.49 g) as an oil.

What is claimed is:

1. A process for preparing a compound of formula (II):

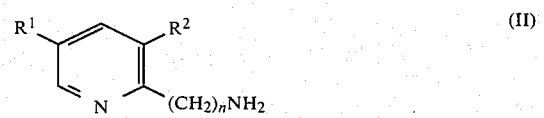

and salts thereof where one of $R^1$ and $R^2$ is $C_{1-4}$ alkyl, the other is bromo and n is from 3 to 5 which comprises reacting a salt of a compound of formula (III):

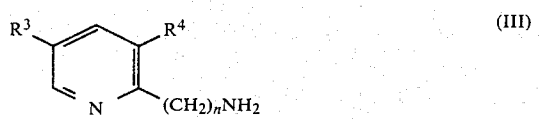

where one of $R^3$ and $R^4$ is $C_{1-4}$ alkyl and the other is hydrogen with an electrophilic brominating agent in an oxidizing polar medium.

2. A process according to claim 1, where the brominating agent is bromine in oleum.

3. A process according to claim 2, wherein $R^4$ is methyl.

4. A process according to claims 1, 2 or 3, where n is 4.

* * * * *